United States Patent
Mayer et al.

(10) Patent No.: US 11,812,970 B2
(45) Date of Patent: Nov. 14, 2023

(54) VASCULAR-MALFORMATION IMPLANT SYSTEM

(71) Applicant: ENDOSTREAM MEDICAL LTD., Or Akiva (IL)

(72) Inventors: Danel Mayer, Tel Aviv (IL); Alon May, Caesarea (IL)

(73) Assignee: ENDOSTREAM MEDICAL LTD., Or Akiva (IL)

( * ) Notice: Subject to any disclaimer, the term of this patent is extended or adjusted under 35 U.S.C. 154(b) by 301 days.

(21) Appl. No.: 17/419,508

(22) PCT Filed: Jan. 16, 2020

(86) PCT No.: PCT/IL2020/050071
§ 371 (c)(1),
(2) Date: Jun. 29, 2021

(87) PCT Pub. No.: WO2020/148768
PCT Pub. Date: Jul. 23, 2020

(65) Prior Publication Data
US 2022/0087685 A1 Mar. 24, 2022

Related U.S. Application Data

(60) Provisional application No. 62/793,532, filed on Jan. 17, 2019.

(51) Int. Cl.
*A61B 17/12* (2006.01)

(52) U.S. Cl.
CPC .. *A61B 17/12145* (2013.01); *A61B 17/12113* (2013.01); *A61B 2017/12054* (2013.01)

(58) Field of Classification Search
CPC .......... A61B 17/1214; A61B 17/12022; A61B 2017/1205; A61B 2017/12054;
(Continued)

(56) References Cited

U.S. PATENT DOCUMENTS

| | | |
|---|---|---|
| 5,350,397 A | 9/1994 | Palermo et al. |
| 5,649,949 A | 7/1997 | Wallace et al. |

(Continued)

FOREIGN PATENT DOCUMENTS

| | | |
|---|---|---|
| CN | 202136073 U | 2/2012 |
| CN | 203787320 U | 8/2014 |

(Continued)

OTHER PUBLICATIONS

An English Translation of an Office Action dated Jun. 2, 2020, which issued during the prosecution of Chinese Patent Application No. 201780051968.9.

(Continued)

*Primary Examiner* — Timothy J Neal
*Assistant Examiner* — Moira E Hayes
(74) *Attorney, Agent, or Firm* — Sughrue Mion, PLLC

(57) ABSTRACT

A delivery tool includes a tubular distal tip fixed to a distal end of a delivery tube. A retention portion of an implant wire of an implant is removably disposed within the tubular distal tip. A pull wire has a distal end portion that is shaped so as to define a pull-wire loop and is removably disposed partially within the delivery tube. A safety wire is removably disposed partially within the tubular distal tip, with a distal portion of the safety wire passing through a tip distal opening. The safety wire has a proximal end portion that is shaped so as to define a safety-wire hook hooked on the pull-wire loop. Proximal pulling on the pull wire proximally retracts the safety wire from the tip distal opening, thereby allowing the retention portion to pass through the tubular distal tip. Other embodiments are also described.

20 Claims, 6 Drawing Sheets

(58) Field of Classification Search
CPC ........ A61B 17/12145; A61B 17/12113; A61B 17/12118

See application file for complete search history.

(56) References Cited

U.S. PATENT DOCUMENTS

| | | |
|---|---|---|
| 5,749,891 A | 5/1998 | Ken et al. |
| 5,935,148 A | 8/1999 | Villar et al. |
| 6,036,720 A | 3/2000 | Abrams et al. |
| 6,306,141 B1 | 10/2001 | Jervis |
| 6,338,736 B1 | 1/2002 | Boosfeld et al. |
| 6,371,972 B1 | 4/2002 | Wallace et al. |
| 6,383,174 B1 | 5/2002 | Eder |
| 6,506,204 B2 | 1/2003 | Mazzocchi |
| 6,551,305 B2 | 4/2003 | Ferrera et al. |
| 6,589,265 B1 | 7/2003 | Palmer et al. |
| 6,740,096 B2 | 5/2004 | Teague et al. |
| 6,790,218 B2 | 9/2004 | Jayaraman |
| 7,128,736 B1 | 10/2006 | Abrams et al. |
| 7,229,461 B2 | 6/2007 | Chin et al. |
| 7,323,000 B2 | 1/2008 | Monstdt et al. |
| 7,377,932 B2 | 5/2008 | Mitelberg et al. |
| 7,569,066 B2 | 8/2009 | Gerberding et al. |
| 8,007,509 B2 | 8/2011 | Buiser et al. |
| 8,333,796 B2 | 12/2012 | Tompkins et al. |
| 8,444,667 B2 | 5/2013 | Porter |
| 8,518,064 B2 | 8/2013 | Kurrus et al. |
| 8,570,343 B2 | 10/2013 | Halstead |
| 8,747,454 B2 | 6/2014 | Khairkhahan et al. |
| 8,764,772 B2 | 7/2014 | Tekulve |
| 8,906,057 B2 | 12/2014 | Connor et al. |
| 9,138,232 B2 | 9/2015 | Connor |
| 9,592,121 B1 | 3/2017 | Khairkhahan |
| 9,629,635 B2 | 4/2017 | Hewitt et al. |
| 2002/0013571 A1 | 1/2002 | Goldfarb et al. |
| 2002/0049468 A1 | 4/2002 | Streeter et al. |
| 2002/0107534 A1 | 8/2002 | Schaefer et al. |
| 2002/0169473 A1 | 11/2002 | Sepetka et al. |
| 2003/0055451 A1 | 3/2003 | Jones et al. |
| 2003/0216772 A1 | 11/2003 | Konya et al. |
| 2004/0034386 A1 | 2/2004 | Fulton et al. |
| 2004/0078054 A1 | 4/2004 | Biggs et al. |
| 2004/0098027 A1 | 5/2004 | Teoh et al. |
| 2004/0167597 A1 | 8/2004 | Costantino et al. |
| 2005/0038460 A1 | 2/2005 | Jayaraman |
| 2005/0107823 A1 | 5/2005 | Leone et al. |
| 2005/0187564 A1 | 8/2005 | Jayaraman |
| 2006/0155323 A1 | 7/2006 | Porter et al. |
| 2006/0206199 A1 | 9/2006 | Churchwell et al. |
| 2006/0276825 A1 | 12/2006 | Mitelberg et al. |
| 2007/0083230 A1 | 4/2007 | Javois |
| 2007/0123928 A1 | 5/2007 | Farnan |
| 2007/0150045 A1 | 6/2007 | Ferrera |
| 2008/0114436 A1 | 5/2008 | Dieck et al. |
| 2008/0119887 A1* | 5/2008 | Que ................. A61B 17/12022 606/103 |
| 2008/0300616 A1 | 12/2008 | Que et al. |
| 2009/0099647 A1 | 4/2009 | Glimsdale et al. |
| 2009/0105653 A1 | 4/2009 | Spenser et al. |
| 2009/0216265 A1 | 8/2009 | DeVries et al. |
| 2009/0312748 A1* | 12/2009 | Johnson ........... A61B 17/12022 606/1 |
| 2010/0121350 A1 | 5/2010 | Mirigian |
| 2010/0174269 A1* | 7/2010 | Tompkins ........ A61B 17/12022 604/507 |
| 2011/0022149 A1 | 1/2011 | Cox et al. |
| 2012/0071911 A1 | 3/2012 | Sadasivan et al. |
| 2012/0143237 A1 | 6/2012 | Cam et al. |
| 2014/0180377 A1 | 6/2014 | Bose et al. |
| 2017/0135701 A1 | 5/2017 | Beckham et al. |
| 2017/0150971 A1 | 6/2017 | Hines |
| 2017/0333678 A1 | 11/2017 | Bowman et al. |
| 2017/0367708 A1 | 12/2017 | Mayer et al. |

FOREIGN PATENT DOCUMENTS

| | | | |
|---|---|---|---|
| WO | 92/21400 A1 | 12/1992 | |
| WO | 2007/121405 A2 | 10/2007 | |
| WO | WO-2007121405 A2 * | 10/2007 | ....... A61B 17/12022 |
| WO | 2008/112435 A2 | 9/2008 | |
| WO | 2012/158883 A1 | 11/2012 | |
| WO | 2014/165256 A2 | 10/2014 | |
| WO | 2016/108241 A1 | 7/2016 | |
| WO | 2017/070171 A1 | 4/2017 | |
| WO | 2017/221252 A1 | 12/2017 | |
| WO | 2020/136643 A2 | 7/2020 | |

OTHER PUBLICATIONS

An EP Communication in Appl. No. 17814898.7, dated Oct. 5, 2020.
An Invitation to pay additional fees dated Mar. 30, 2020, which issued during the prosecution of Applicant's PCT/IL2019/051401.
An ISR and Written Opinion issued in PCT/IL2019/051401, dated Jun. 24, 2020.
Communication dated Oct. 21, 2019 from the United State Patent and Trademark Office in U.S. Appl. No. 15/540,664.
Communication dated Feb. 3, 2020 by the European Patent Office in application No. 17814898.7.
Nit-Occlud PDA, pfm medical (Jun. 2012).
Medtronic EV3 Axium Youtube excerpts downloaded Aug. 13, 2018.
An International Search Report and a Written Opinion both dated Oct. 3, 2017, which issued during the prosecution of Applicant's PCT/IL2017/050694.
An International Search Report and a Written Opinion both dated Apr. 19, 2016, which issued during the prosecution of Applicant's PCT/IL2015/051271.
U.S. Appl. No. 62/352,578, filed Jun. 21, 2016.
U.S. Appl. No. 62/444,963, filed Jan. 11, 2017.
Office Action dated Sep. 2, 2020, issued by the United States Patent and Trademark Office in U.S. Appl. No. 16/311,744.
Notice of Allowance dated Dec. 14, 2020, issued by the United States Patent and Trademark Office in U.S. Appl. No. 16/311,744.
An International Search Report and a Written Opinion both dated Mar. 30, 2020, which issued during the prosecution of Applicant's PCT/IL2020/050071.

* cited by examiner

VASCULAR-MALFORMATION IMPLANT SYSTEM

CROSS-REFERENCE TO RELATED APPLICATIONS

The present application is the U.S. national stage of International Application PCT/IL2020/050071, filed Jan. 16, 2020, which claims priority from U.S. Provisional Application 62/793,532, filed Jan. 17, 2019, which is assigned to the assignee of the present application and incorporated herein by reference.

FIELD OF THE APPLICATION

The present invention relates generally to minimally-invasive techniques for treating vascular malformations such as aneurysms.

BACKGROUND OF THE APPLICATION

An aneurysm is an abnormal local dilation of an artery caused by a weakening of the artery wall. In the past, cerebral aneurysms were frequently treated by direct surgical intervention, such as by installing a clip around the base of the aneurysm to prevent passage of blood between the aneurysm and the lumen of the vessel. Attempts have then been made to develop minimally-invasive techniques for treating such aneurysms, for example, by filling the aneurysm with endovascular embolization coils, such that the aneurysm eventually becomes a solid mass of coils and thrombus.

SUMMARY OF THE APPLICATION

Applications of the present invention provide an implant system that comprises an implant and a delivery tool for delivering the implant to a site within a patient. The implant is configured to treat a vascular malformation, such as an aneurysm. The implant typically comprises an implant wire, which includes (a) a coil-wire portion having a coil-wire-portion diameter and (b) a proximal end portion that (1) includes a proximal end of the implant wire, (2) is non-axially-overlapping with the coil-wire portion, and (3) includes a retention portion that has a retention diameter that is greater than the coil-wire-portion diameter; and a coil, which is coiled around the coil-wire portion and not the proximal end portion of the implant wire.

The delivery tool typically comprises a delivery tube; a tubular distal tip, which is (a) fixed to a distal end of the delivery tube, (b) shaped so as to define a tip distal opening, and (c) tapers toward the tip distal opening (the retention portion is removably disposed within the tubular distal tip); and a safety wire.

The safety wire is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip.

The implant system is configured such that proximal pulling (i.e., to the left in the figures) on the safety wire proximally retracts the safety wire from the tip distal opening of the tubular distal tip, thereby allowing the retention portion to pass through the tip distal opening (by increasing the effective available size of the tip distal opening). This allows releasing of the retention portion (and thus the implant) from the tubular distal tip. Because the tapered axial portion of the tubular distal tip is smooth, it does not snag any sharp edges of the retention portion, like a conventional distal retention ring might.

For some applications, the delivery tool further comprises a pull wire, which is coupled to the safety wire and is removably disposed partially within the delivery tube. The implant system is configured such that proximal pulling on the pull wire proximally pulls the safety wire.

For some applications, the safety wire has a proximal end portion that is shaped so as to define a safety-wire hook. The pull wire has a distal end portion that is shaped so as to define a pull-wire loop. The safety-wire hook is hooked on the pull-wire loop.

Typically, during advancement of the tube through the vasculature, a proximal portion of the pull wire and a proximal portion of the tube are fixed to each other, e.g., by crimping, in order to minimize relative axial movement between the pull wire and the tube during advancement of the tube. The unpredictable tortuosity of the vasculature (e.g., the brain vasculature) may cause inadvertent relative axial movement between the pull wire and the tube. This relative axial movement may have the effect of shortening the pull wire, resulting in pulling the distal portion of the safety wire through the tip distal opening, thereby prematurely releasing the implant from the delivery tool. The pull-wire loop provides some slack to absorb some of this proximal pulling of the pull wire. Typically, in order to provide this slack, a distal-most point of the pull-wire loop is initially disposed distal to a proximal-most point of the safety-wire hook, such as a distance equal to at least 1 mm, e.g., at least 2, 3, or 4 mm distal to the proximal-most point of the safety-wire hook. As a result, proximal pulling of the pull wire by up to the distance is not transmitted to the distal portion of the safety wire.

For some applications, the safety wire is shaped so as to define a helical portion, which, when unconstrained, has an unconstrained helical-portion outer diameter that is greater than a greatest inner diameter of the tubular distal tip. As a result, the helical portion, when removably disposed within the tubular distal tip, pushes radially outwardly against an inner wall of the tubular distal tip.

The helical portion may help lock the safety wire in place until the pull wire is proximally pulled, even if, for example, the coil of the implant pushes the retention portion of the safety wire proximally. For example, the turns of the coil may repeatedly push on the distal tip of the safety wire as the system is advanced through the vasculature. This proximally-directed pushing on the helical portion increases the diameter of the helix, thereby increasing the force applied by the helix to the inner wall of the tubular distal tip and enhancing locking.

In some applications of the present invention, a method is provided for assembling an implant system. The method comprises disposing the pull wire of the delivery tool partially within the delivery tube of the delivery tool. The retention portion of the proximal end portion of the implant wire of the implant is inserted (a) through the tip distal opening of the tubular distal tip and (b) into the tubular distal tip. Utilizing a lateral access window defined by a wall of the tubular distal tip, the safety-wire hook is hooked onto the pull-wire loop. A distal portion of the safety wire is inserted through the lateral access window and into the tubular distal tip. The distal portion of the safety wire is removably disposed through the tip distal opening so as to effectively reduce a size of the tip distal opening to be too small for the retention portion to pass through, thereby retaining the retention portion within the tubular distal tip.

There is therefore provided, in accordance with an application of the present invention, an implant system including:
(a) an implant, which includes:
(i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and
(ii) a coil, which is coiled around the coil-wire portion and not the proximal end portion of the implant wire; and
(b) a delivery tool, which includes:
(i) a delivery tube;
(ii) a tubular distal tip, which is (A) fixed to a distal end of the delivery tube, (B) shaped so as to define a tip distal opening, and (C) tapers toward the tip distal opening, wherein the retention portion is removably disposed within the tubular distal tip; and
(iii) a safety wire, which is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip,
wherein the implant system is configured such that proximal pulling on the safety wire proximally retracts the safety wire from the tip distal opening, thereby allowing the retention portion to pass through the tubular distal tip.

For some applications, an opening inner diameter of the tip distal opening equals between 30% and 70% of a greatest outer diameter of the tubular distal tip.

For some applications, an opening inner diameter of the tip distal opening is between 0.2 and 0.5 mm.

For some applications, a greatest outer diameter of the delivery tube is between 0.25 and 0.7 mm.

For some applications, the safety wire is removably disposed partially within the tubular distal tip, with the distal portion of the safety wire passing through the tip distal opening and through a portion of the coil alongside a portion of the coil-wire portion of the implant wire. For some applications, a length of the portion of the coil-wire portion alongside which the safety wire passes is between 0.1 and 3 mm.

For some applications, the retention diameter equals at least 125% of the coil-wire-portion diameter.

For some applications, the implant includes a retention element, which is fixed to the proximal end portion of the implant wire so as to define the retention portion having the retention diameter. For some applications, the retention element is cylindrical. For some applications, the cylindrical retention element has a length of between 0.2 and 0.8 mm and a diameter of between 0.12 and 0.55 mm. For some applications, the retention element is spherical.

For some applications, the implant includes an intravascular coil.

For some applications, the implant includes an orifice section; a docking section; and a connecting section, and the implant is configured such that, when unconstrained, the orifice section is shaped so as to define an orifice-section curve, the docking section is shaped so as to define a docking-section curve, and the connecting section connects the orifice-section curve with the docking-section curve.

For some applications:
the delivery tool further includes a pull wire, which is coupled to the safety wire and is removably disposed partially within the delivery tube, and
the implant system is configured such that proximal pulling on the pull wire proximally pulls the safety wire.

For some applications:
the safety wire has a proximal end portion that is shaped so as to define a safety-wire hook,
the pull wire has a distal end portion that is shaped so as to define a pull-wire loop, and
the safety-wire hook is hooked on the pull-wire loop.

There is further provided, in accordance with an application of the present invention, an implant system including:
(a) an implant, which includes:
(i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and
(ii) a coil, which is coiled around the coil-wire portion and not the proximal end portion of the implant wire; and
(b) a delivery tool, which includes:
(i) a delivery tube;
(ii) a tubular distal tip, which is (A) fixed to a distal end of the delivery tube and (B) shaped so as to define a tip distal opening, wherein the retention portion is removably disposed within the tubular distal tip; and
(iii) a safety wire, which (A) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip, and (B) is shaped so as to define a helical portion, which, when unconstrained, has an unconstrained helical-portion outer diameter that is greater than a greatest inner diameter of the tubular distal tip, such that the helical portion, when removably disposed within the tubular distal tip, pushes radially outwardly against an inner wall of the tubular distal tip,
wherein the implant system is configured such that proximal pulling on the safety wire proximally retracts the safety wire from the tip distal opening, thereby allowing the retention portion to pass through the tubular distal tip.

For some applications, the unconstrained helical-portion outer diameter is between 0.2 and 0.7 mm.

For some applications, the unconstrained helical-portion outer diameter is between 100% and 150% of the greatest inner diameter of the tubular distal tip.

For some applications, the greatest inner diameter of the tubular distal tip is between 0.15 and 0.65 mm.

For some applications, the helical portion has between 1.25 and 10 turns, such as between 2 and 3 turns, when unconstrained.

For some applications, the unconstrained helical-portion outer diameter is constant along the helical portion when unconstrained.

For some applications, the safety wire is removably disposed partially within the tubular distal tip, with the distal portion of the safety wire passing through the tip distal opening and through a portion of the coil alongside a portion of the coil-wire portion of the implant wire. For some applications, a length of the portion of the coil-wire portion alongside which the safety wire passes is between 0.1 and 3 mm.

For some applications, a greatest outer diameter of the delivery tube is between 0.25 and 0.7 mm.

For some applications, the retention diameter equals at least 125% of the coil-wire-portion diameter.

For some applications, the tubular distal tip tapers toward the tip distal opening.

For some applications, the implant includes a retention element, which is fixed to the proximal end portion of the implant wire so as to define the retention portion having the retention diameter. For some applications, the retention element is cylindrical. For some applications, the cylindrical retention element has a length of between 0.2 and 0.8 mm and a diameter of between 0.12 and 0.55 mm. For some applications, the retention element is spherical.

For some applications, the implant includes an intravascular coil.

For some applications, the implant includes an orifice section; a docking section; and a connecting section, and the implant is configured such that, when unconstrained, the orifice section is shaped so as to define an orifice-section curve, the docking section is shaped so as to define a docking-section curve, and the connecting section connects the orifice-section curve with the docking-section curve.

For some applications:
the delivery tool further includes a pull wire, which is coupled to the safety wire and is removably disposed partially within the delivery tube, and
the implant system is configured such that proximal pulling on the pull wire proximally pulls the safety wire.

For some applications:
the safety wire has a proximal end portion that is shaped so as to define a safety-wire hook,
the pull wire has a distal end portion that is shaped so as to define a pull-wire loop, and
the safety-wire hook is hooked on the pull-wire loop.

There is still further provided, in accordance with an application of the present invention, an implant system including:
(a) an implant, which includes:
(i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and
(ii) a coil, which is coiled around the coil-wire portion and not the proximal end portion of the implant wire; and
(b) a delivery tool, which includes:
(i) a delivery tube;
(ii) a tubular distal tip, which is (A) fixed to a distal end of the delivery tube and (B) shaped so as to define a tip distal opening, wherein the retention portion is removably disposed within the tubular distal tip;
(iii) a safety wire, which (A) has a proximal end portion that is shaped so as to define a safety-wire hook and (B) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip; and
(iv) a pull wire, which (A) has a distal end portion that is shaped so as to define a pull-wire loop and (B) is removably disposed partially within the delivery tube, wherein the safety-wire hook is hooked on the pull-wire loop,
wherein the implant system is configured such that proximal pulling on the pull wire proximally retracts the safety wire from the tip distal opening, thereby allowing the retention portion to pass through the tubular distal tip.

For some applications, the safety wire is removably disposed partially within the tubular distal tip, with the distal portion of the safety wire passing through the tip distal opening and through a portion of the coil alongside a portion of the coil-wire portion of the implant wire. For some applications, a length of the portion of the coil-wire portion alongside which the safety wire passes is between 0.1 and 3 mm.

For some applications, the safety wire is shaped so as to define a helical portion, which, when unconstrained, has an unconstrained helical-portion outer diameter that is greater than a greatest inner diameter of the tubular distal tip, such that the helical portion, when removably disposed within the tubular distal tip, pushes radially outwardly against an inner wall of the tubular distal tip.

For some applications, the retention diameter equals at least 125% of the coil-wire-portion diameter.

For some applications, the pull wire is coated with a non-stick coating and the safety wire is not coated with a non-stick coating.

For some applications, a greatest outer diameter of the delivery tube is between 0.25 and 0.7 mm.

For some applications, the tubular distal tip tapers toward the tip distal opening.

For some applications, the coil has an outer dimeter of between 0.24 and 0.69 mm when unconstrained.

For some applications, the implant includes a retention element, which is fixed to the proximal end portion of the implant wire so as to define the retention portion having the retention diameter. For some applications, the retention element is cylindrical. For some applications, the cylindrical retention element has a length of between 0.2 and 0.8 mm and a diameter of between 0.12 and 0.55 mm. For some applications, the retention element is spherical.

For some applications, the implant includes an intravascular coil.

For some applications, the implant includes an orifice section; a docking section; and a connecting section, and the implant is configured such that, when unconstrained, the orifice section is shaped so as to define an orifice-section curve, the docking section is shaped so as to define a docking-section curve, and the connecting section connects the orifice-section curve with the docking-section curve.

There is additionally provided, in accordance with an application of the present invention, a method for treating a vascular malformation, the method including:
inserting a microcatheter into a blood vessel while a delivery tool and an implant of an implant system are removably disposed in the microcatheter, with a proximal end of the implant removably coupled to a tubular distal tip of the delivery tool,
wherein the implant includes (i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and (ii) a coil, which is coiled around the coil-wire portion and not the proximal end portion of the implant wire, and wherein the delivery tool includes (i) a delivery tube; (ii) a tubular distal tip, which is (A) fixed to a distal end of the delivery tube, (B) shaped so as to define a tip distal opening, and (C) tapers toward the tip distal opening, wherein the retention portion is removably disposed within the tubular distal tip; and (iii) a safety wire, which (A) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip;

advancing the microcatheter in the blood vessel toward the vascular malformation;

deploying the implant from the microcatheter into the vascular malformation; and releasing the implant from the delivery tool by proximally pulling on the safety wire so as to proximally retract the safety wire from the tip distal opening of the tubular distal tip, thereby allowing the retention portion to pass through the tip distal opening.

There is yet additionally provided, in accordance with an application of the present invention, a method for treating a vascular malformation, the method including:

inserting a microcatheter into a blood vessel while a delivery tool and an implant of an implant system are removably disposed in the microcatheter, with a proximal end of the implant removably coupled to a tubular distal tip of the delivery tool, wherein the implant includes (i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and (ii) a coil, which is coiled around the coil-wire portion and not the proximal end portion of the implant wire, and wherein the delivery tool includes (i) a delivery tube; (ii) a tubular distal tip, which is (A) fixed to a distal end of the delivery tube and (B) shaped so as to define a tip distal opening, wherein the retention portion is removably disposed within the tubular distal tip; and (iii) a safety wire, which (A) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip, and (B) is shaped so as to define a helical portion, which, when unconstrained, has an unconstrained helical-portion outer diameter that is greater than a greatest inner diameter of the tubular distal tip, such that the helical portion, when removably disposed within the tubular distal tip, pushes radially outwardly against an inner wall of the tubular distal tip;

advancing the microcatheter in the blood vessel toward the vascular malformation;

deploying the implant from the microcatheter into the vascular malformation; and releasing the implant from the delivery tool by proximally pulling on the safety wire so as to proximally retract the safety wire from the tip distal opening of the tubular distal tip, thereby allowing the retention portion to pass through the tip distal opening.

There is also provided, in accordance with an application of the present invention, a method for treating a vascular malformation, the method including:

inserting a microcatheter into a blood vessel while a delivery tool and an implant of an implant system are removably disposed in the microcatheter, with a proximal end of the implant removably coupled to a tubular distal tip of the delivery tool, wherein the implant includes (i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and (ii) a coil, which is coiled around the coil-wire portion and not the proximal end portion of the implant wire, and wherein the delivery tool includes (i) a delivery tube; (ii) a tubular distal tip, which is (A) fixed to a distal end of the delivery tube and (B) shaped so as to define a tip distal opening, wherein the retention portion is removably disposed within the tubular distal tip; (iii) a safety wire, which (A) has a proximal end portion that is shaped so as to define a safety-wire hook and (B) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip; and (iv) a pull wire, which (A) has a distal end portion that is shaped so as to define a pull-wire loop and (B) is removably disposed partially within the delivery tube, wherein the safety-wire hook is hooked on the pull-wire loop;

advancing the microcatheter in the blood vessel toward the vascular malformation;

deploying the implant from the microcatheter into the vascular malformation; and releasing the implant from the delivery tool by proximally pulling on the safety wire so as to proximally retract the safety wire from the tip distal opening of the tubular distal tip, thereby allowing the retention portion to pass through the tip distal opening.

There is further provided, in accordance with an application of the present invention, a method for assembling an implant system, the method including:

disposing a pull wire of a delivery tool partially within a delivery tube of the delivery tool;

inserting a retention portion of a proximal end portion of an implant wire of an implant (a) through a tip distal opening of a tubular distal tip that is fixed to a distal end of the delivery tube and (b) into the tubular distal tip, wherein the implant wire further includes a coil-wire portion having a coil-wire-portion diameter, wherein the proximal end portion of the implant wire (a) includes a proximal end of the implant wire and (b) is non-axially-overlapping with the coil-wire portion, wherein the retention portion has a retention diameter that is greater than the coil-wire-portion diameter, and wherein a coil of the implant is coiled around the coil-wire portion and not the proximal end portion of the implant wire;

utilizing a lateral access window defined by a wall of the tubular distal tip, hooking a safety-wire hook defined by a proximal end portion of the safety wire onto the pull-wire loop;

inserting a distal portion of a safety wire through the lateral access window and into the tubular distal tip; and removably disposing the distal portion of the safety wire through the tip distal opening so as to effectively reduce a size of the tip distal opening to be too small for the retention portion to pass through, thereby retaining the retention portion within the tubular distal tip.

For some applications, inserting the distal portion of the safety wire through the lateral access window and into the tubular distal tip includes inserting the distal portion of the safety wire through the lateral access window and into the tubular distal tip before hooking the safety-wire hook onto the pull-wire loop.

For some applications, hooking the safety-wire hook onto the pull-wire loop includes hooking the safety-wire hook onto the pull-wire loop while (a) the pull wire is partially disposed within the delivery tube and (b) the pull-wire loop and the safety-wire hook are disposed at least partially inside the delivery tool.

For some applications, hooking the safety-wire hook onto the pull-wire loop includes hooking the safety-wire hook onto the pull-wire loop while the pull-wire loop is at least partially axially aligned with the lateral access window.

For some applications, removably disposing the distal portion of the safety wire includes removably disposing the distal portion of the safety wire through the tip distal opening and through a portion of the coil alongside a portion of the coil-wire portion of the implant wire.

The present invention will be more fully understood from the following detailed description of embodiments thereof, taken together with the drawings, in which:

DETAILED DESCRIPTION OF APPLICATIONS

Figure 1:
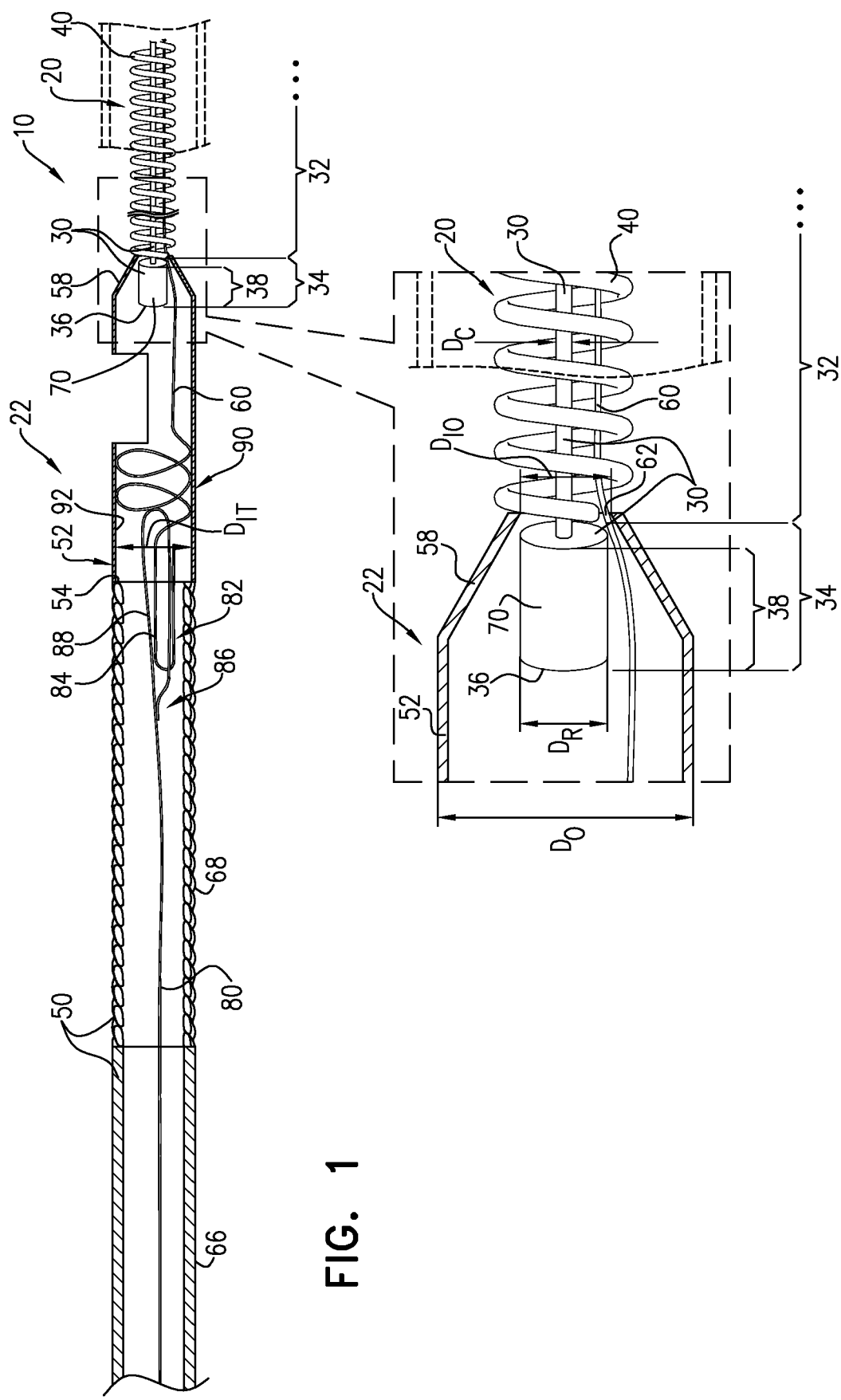
FIG. 1 is a schematic illustration of an implant system, in accordance with an application of the present invention.

FIG. 1 is a schematic illustration of an implant system 10, in accordance with an application of the present invention. Implant system 10 comprises an implant 20 and a delivery tool 22 for delivering implant 20 to a site within a patient, such as described hereinbelow with reference to FIGS. 3A-D. FIG. 1 shows a portion of implant 20; the full implant can be seen in FIGS. 3A-D, described hereinbelow.

Figure 2A:
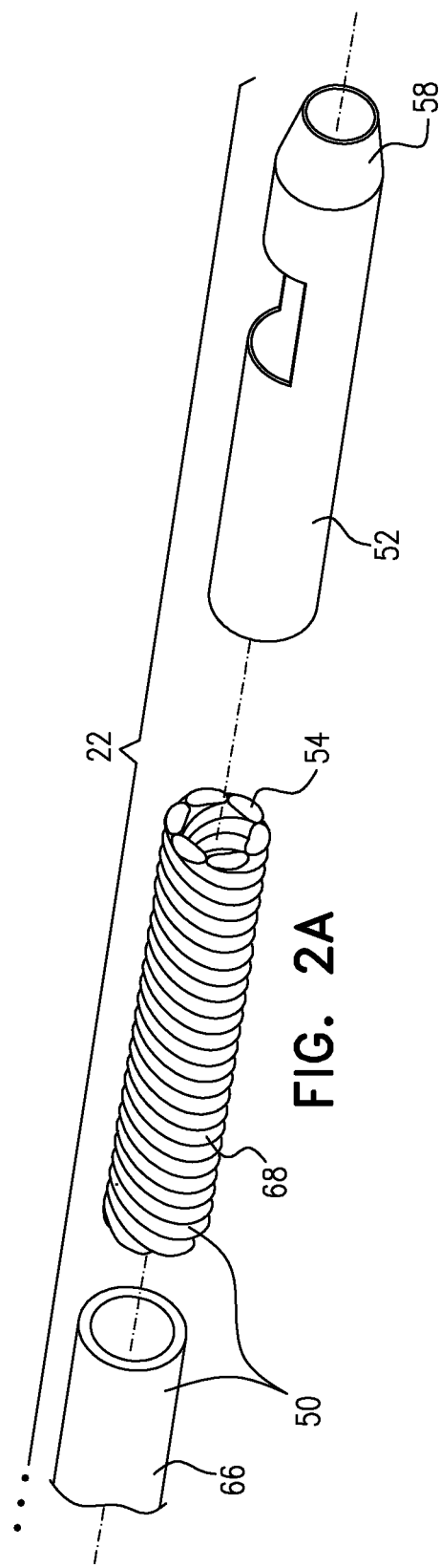
FIGS. 2A-B are schematic exploded and assembled views of a delivery tool of the implant system of FIG. 1, in accordance with an application of the present invention.
Figure 2B:
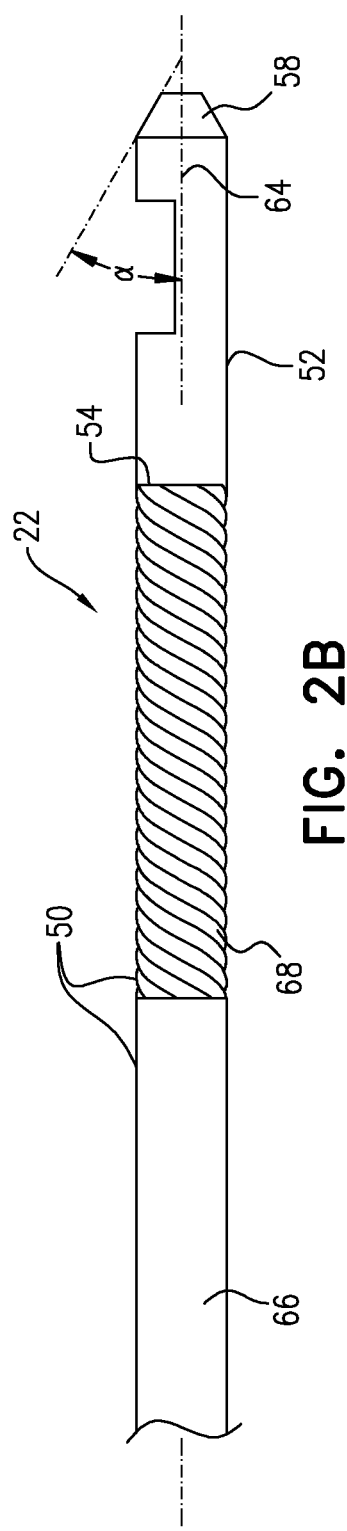
Figure 2C:
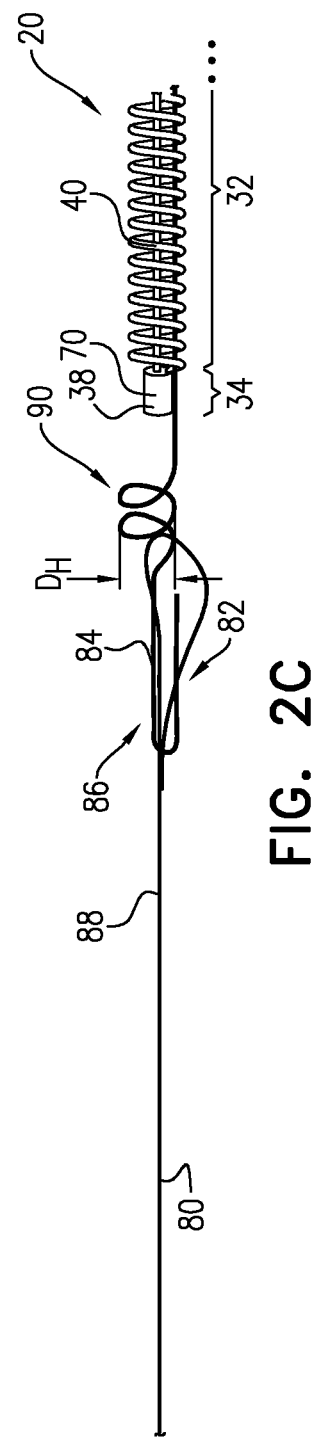
FIG. 2C is a schematic illustration of a portion of a delivery tool and a portion of an implant of the implant system of FIG. 1.

Reference is still made to FIG. 1 and is additionally made to FIGS. 2A-C. FIGS. 2A-B are schematic exploded and assembled views of delivery tool 22, respectively, in accordance with an application of the present invention. FIG. 2C is a schematic illustration of a portion of delivery tool 22 and a portion of implant 20.

Implant 20 is configured to treat a vascular malformation, such as an aneurysm. For some applications, implant 20 is configured to bridge the neck of a vascular malformation, such as an aneurysm, e.g., a wide-necked aneurysm, in order to prevent coil herniation. For example, the aneurysm may be a saccular aneurysm formed in the wall of a blood vessel, typically an artery, such as a cerebral aneurysm, a coronary artery aneurysm, a ventricular aneurysm, an aneurysm of the sinus of Valsalva, an aneurysm following cardiac surgery, or an aortic aneurysm. Alternatively, the vascular malformation may be any congenital and/or non-congenital blood vessel abnormality, such as, but not limited to, a fistula, a tumor, or an arteriovenous malformation.

For some applications, implant 20 comprises an intravascular coil.

For some applications, implant 20 comprises an orifice section; an intra-vascular-malformation docking section; and a connecting section, and implant 20 is configured such that, when unconstrained, the orifice section is shaped so as to define an orifice-section curve, the intra-vascular-malformation docking section is shaped so as to define a docking-section curve, and the connecting section connects the orifice-section curve with the docking-section curve.

Implant 20 may implement any of the techniques described in the patent applications and patent application publications incorporated hereinbelow by reference.

Implant 20 typically comprises:
an implant wire 30 (comprising, for example, Nitinol), which includes (a) a coil-wire portion 32 having a coil-wire-portion diameter $D_C$ and (b) a proximal end portion 34 that (1) includes a proximal end 36 of implant wire 30, (2) is non-axially-overlapping with coil-wire portion 32, and (3) includes a retention portion 38 that has a retention diameter $D_R$ that is greater than the coil-wire-portion diameter $D_C$; and
a coil 40, which is coiled around coil-wire portion 32 and not proximal end portion 34 of implant wire 30.

Delivery tool 22 typically comprises:
a delivery tube 50;
a tubular distal tip 52, which is (a) fixed to a distal end 54 of delivery tube 50, (b) shaped so as to define a tip distal opening 56, and (c) tapers toward tip distal opening 56 (along a tapered axial portion 58 of tubular distal tip 52); retention portion 38 is removably disposed within tubular distal tip 52; and
a safety wire 60.

Safety wire 60 is removably disposed partially within tubular distal tip 52, with a distal portion 62 of safety wire 60 passing through tip distal opening 56 so as to effectively reduce a size of tip distal opening 56 to be too small for retention portion 38 to pass through, thereby retaining retention portion 38 within tubular distal tip 52.

Implant system 10 is configured such that proximal pulling (i.e., to the left in the figures) on safety wire 60 proximally retracts safety wire 60 from tip distal opening 56 of tubular distal tip 52, thereby allowing retention portion 38 to pass through tip distal opening 56 (by increasing the effective available size of tip distal opening 56). This allows releasing of retention portion 38 (and thus implant 20) from tubular distal tip 52, such as described hereinbelow with reference to FIG. 3B.

Because tapered axial portion 58 of tubular distal tip 52 is smooth, it does not snag any sharp edges of retention portion 38, like a conventional distal retention ring might. For some applications, tapered axial portion 58 defines an angle a (alpha) of between 20 and 70 degrees (e.g., between 30 and 60 degrees) with a central longitudinal axis 64 of tubular distal tip 52 (labeled in FIG. 2B). Optionally, tapered axial portion 58 is manufacturing by swaging, in which case the tapered portion is at least partially curved and thus does define a constant angle with the central longitudinal axis. Alternatively, tapered axial portion 58 is manufactured using a non-swaging manufacturing process.

For some applications, the retention diameter $D_R$ equals at least 125% of the coil-wire-portion diameter $D_C$, such as at least 200% of the coil-wire-portion diameter $D_C$.

For some applications, safety wire 60 is removably disposed partially within tubular distal tip 52, with distal portion 62 of safety wire 60 passing through tip distal S opening 56 and through a portion of coil 40 alongside a portion of coil-wire portion 32 of implant wire 30, such as shown in FIGS. 1 and 2C. For example, a length of the portion of coil-wire portion 32 alongside which safety wire 60 passes may be at least 0.1 mm, no more than 3 mm, and/or between 0.1 and 3 mm.

For some applications, coil 40 has an outer diameter $D_{OC}$ (labeled in FIG. 2C) of at least 300% of the coil-wire-portion diameter $D_C$, no more than 900% of the coil-wire-portion diameter $D_C$, and/or between 300% and 900% of the coil-wire-portion diameter $D_C$. Alternatively or additionally, for some applications, coil 40 has an outer diameter $D_{OC}$ (labeled in FIG. 2C) of at least between 0.24 mm, no more than 0.69 mm, and/or between 0.3 and 0.4 mm, e.g., about 0.36 mm.

(For applications in which implant 20 comprises orifice and intra-vascular-malformation docking sections having orifice-section and docking-section curves, respectively, such as described above, these curves are of a much larger scale than that of coil 40. These larger curves are defined by shaping coil 40 together with coil-wire portion 32 of implant wire 30 into a larger-scale curve. In other words, coil 40 may be considered a primary coil and the curves may be considered secondary coils.)

Reference is still made to FIGS. 1 and 2A-C. For some applications, implant 20 comprises a retention element 70, which is fixed to proximal end portion 34 of implant wire 30 so as to define retention portion 38 having the retention diameter. As used in the present application, including in the claims, retention element 70 is considered a portion of implant wire 30, even if retention element 70 is fabricated as a separate piece and subsequently attached to the rest of implant wire 30.

For some applications, retention element 70 is cylindrical, such as shown in the figures (and, for example, may be crimped onto implant wire 30). For example, cylindrical retention element 70 may have a length of at least 0.2 mm, no more than 0.8 mm (e.g., no more than 0.4 mm), and/or between 0.2 and 0.8 mm (e.g., between 0.2 and 0.4 mm), and/or a diameter of at least 0.12 mm, no more than 0.55 mm (e.g., no more than 0.4 mm), and/or between 0.12 and 0.55 mm (e.g., between 0.12 and 0.4 mm, e.g., between 0.15 and 0.3 mm, such as 0.2 mm).

For some other applications, retention element 70 is spherical or is formed by balling up implant wire 30 at retention portion 38 (configurations not shown). For yet other applications, a proximal end portion of retention element 70 is rounded, e.g., semispherical (configuration not shown), and, optionally, a distal end portion of retention element 70 is cylindrical (as shown).

For some applications, an opening inner diameter $D_{IO}$ of tip distal opening 56 equals at least 30%, no more than 70%, and/or between 30% and 70% of a greatest outer diameter $D_O$ of tubular distal tip 52 (labeled in FIG. 1). Alternatively or additionally, for some applications, the opening inner diameter $D_{IO}$ of tip distal opening 56 is at least 0.2 mm, no more than 0.5 mm, and/or between 0.2 and 0.5 mm.

For some applications, the greatest outer diameter $D_O$ of delivery tube 50 is at least 0.25 mm, no more than 0.7 min (e.g., no more than 0.5 mm), and/or between 0.25 and 0.7 mm (e.g., between 0.2 and 0.4 mm).

For some applications, delivery tube comprises a proximal hypotube catheter shaft 66 fixed to a distal highly-flexible tube 68. For example, highly-flexible tube 68 may comprise a hollow helical strand (HHS) tube, as shown, a coil (configuration not shown), or a tube having a helical slit (e.g., laser-cut). Distal highly-flexible tube 68 includes the above-mentioned distal end 54 of delivery tube 50 (which is fixed to tubular distal tip 52). Distal highly-flexible tube 68 may provide increased flexibility for navigating the tortuosity of the vasculature (e.g., the brain vasculature). Hypotube catheter shafts are commercially available (e.g., from Johnson Matthey Medical Components, West Chester, Pa., USA), as are HHS tubes (e.g., from Fort Wayne Metals Research Products Corp., Fort Wayne, Ind., USA). Optionally, proximal hypotube catheter shaft 66 and/or distal hollow helical strand (HHS) tube 68 comprise stainless steel.

Reference is still made to FIGS. 1 and 2A-C. For some applications, delivery tool 22 further comprises a pull wire 80, which is coupled to safety wire 60 and is removably disposed partially within delivery tube 50. Implant system 10 is configured such that proximal pulling on the pull wire proximally pulls safety wire 60, such as described hereinbelow with reference to FIG. 3B.

For some applications, such as shown in FIGS. 1 and 2C, safety wire 60 has a proximal end portion 82 that is shaped so as to define a safety-wire hook 84. Pull wire 80 has a distal end portion 86 that is shaped so as to define a pull-wire loop 88. Safety-wire hook 84 is hooked on pull-wire loop 88. Optionally, safety-wire hook 84 is shaped as a complete loop (configuration not shown).

Typically, during advancement of tube 50 through the vasculature, a proximal portion of pull wire 80 and a proximal portion of tube 50 are fixed to each other, e.g., by crimping, in order to minimize relative axial movement between pull wire 80 and tube 50 during advancement of the tube. The unpredictable tortuosity of the vasculature (e.g., the brain vasculature) may cause inadvertent relative axial movement between pull wire 80 and tube 50. This relative axial movement may have the effect of shortening pull wire 80, resulting in pulling distal portion 62 of safety wire 60 through tip distal opening 56, thereby prematurely releasing implant 20 from delivery tool 22. Pull-wire loop 88 provides some slack to absorb some of this proximal pulling of pull wire 80. Typically, in order to provide this slack, a distal-most point of pull-wire loop 88 is initially disposed distal to a proximal-most point of safety-wire hook 84, such as a distance equal to at least 1 mm, e.g., at least 2, 3, or 4 mm distal to the proximal-most point of safety-wire hook 84. As a result, proximal pulling of pull wire 80 by up to the distance is not transmitted to distal portion 62 of safety wire 60.

For some applications, such as shown in FIGS. 1 and 2C, safety wire 60 is shaped so as to define a helical portion 90, which, when unconstrained, has an unconstrained helical-portion outer diameter $D_H$ (labeled in FIG. 2C) that is greater than a greatest inner diameter $D_{IT}$ (labeled in FIG. 1) of tubular distal tip 52. As a result, helical portion 90, when removably disposed within tubular distal tip 52, pushes radially outwardly against an inner wall 92 of tubular distal tip 52.

For some applications, such as shown, the unconstrained helical-portion outer diameter $D_H$ is constant along helical portion 90 when unconstrained, For some applications, helical portion 90 has at least 1.25 turns (e.g., at least 2 turns), no more than 10 turns (e.g., no more than 5 turns, such as no more than 3 turns), and/or between 1.25 and 10 turns, such as between 2 and 5 turns, e.g., between 2 and 3 turns, when unconstrained.

For some applications, wherein the unconstrained helical-portion outer diameter $D_H$ is at least 0.2 mm, no more than 0.7 mm, and/or between 0.2 and 0.7 mm. Alternatively or additionally, for some applications, the unconstrained helical-portion outer diameter $D_H$ is at least 100%, no more than 150%, and/or between 100% and 150% of the greatest inner diameter $D_{IT}$ of tubular distal tip 52. For some applications, the greatest inner diameter $D_{IT}$ of tubular distal tip 52 is at least 0.15 mm, no more than 0.65 mm, and/or between 0.15 and 0.65 mm.

Helical portion 90 may help lock safety wire 60 in place until pull wire 80 is proximally pulled, even if, for example, coil 40 of implant 20 pushes retention portion 38 of safety wire 60 proximally. For example, the turns of coil 40 may repeatedly push on the distal tip of safety wire 60 as the system is advanced through the vasculature. This proximally-directed pushing on helical portion 90 increases the diameter of the helix, thereby increasing the force applied by the helix to inner wall 92 of tubular distal tip 52 and enhancing locking. (This force may be provided in part by configuring the unconstrained helical-portion outer diameter $D_H$ to be greater than the greatest inner diameter $D_{IT}$ of tubular distal tip 52.)

For some applications, pull wire 80 is coated with a non-stick coating (e.g., PTFE) and safety wire 60 is not coated with a non-stick coating. The non-stick coating reduces friction when pull wire 80 is pulled proximally. (The tortuosity of the vasculature (e.g., the brain vasculature) applies substantial friction to pull wire 80.) The lack of coating of safety wire 60 avoids reducing friction between helical portion 90 and inner wall 92 of tubular distal tip 52.

Reference is made to FIGS. 3A-D, which are schematic illustrations of a method of using implant system 10 to treat a vascular malformation, such as an aneurysm 100, in accordance with an application of the present invention.

Figure 3A:
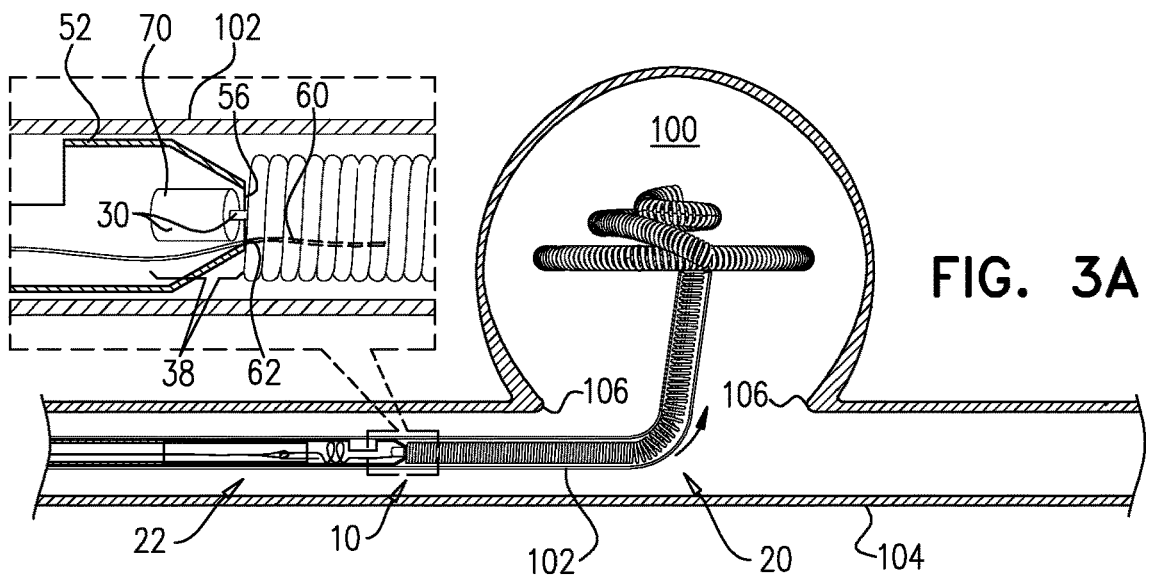
FIGS. 3A-D are schematic illustrations of a method of using the implant system of FIG. 1 to treat a vascular malformation.

Before the state shown in FIG. 3A is reached, a guidewire is inserted into a blood vessel 104 and advanced until a distal end of the guidewire is disposed in aneurysm 100. A microcatheter 102 is inserted into blood vessel 104 and advanced over the guidewire until the distal end of the microcatheter is disposed in aneurysm 100. The guidewire is withdrawn and removed from the subject's body, leaving the distal end of the microcatheter in the aneurysm. Delivery tool 22 and implant 20 are inserted into the microcatheter via a proximal end of the microcatheter, such that delivery tool 22 and implant 20 are removably disposed in the microcatheter, with a proximal end of implant 20 removably coupled to tubular distal tip 52 of delivery tool 22, as described hereinabove with reference to FIGS. 1-2C. Delivery tool 22 is used to push implant 20 out of the distal end of microcatheter 102.

FIG. 3A shows the deployment after implant 20 has been deployed from microcatheter 102 into aneurysm 100, and while the proximal end of implant 20 is still removably coupled to tubular distal tip 52 of delivery tool 22. Distal portion 62 of safety wire 60 passes through tip distal opening 56 so as to effectively reduce a size of tip distal opening 56 to be too small for retention portion 38 of proximal end portion 34 of implant wire 30 to pass through, thereby retaining retention portion 38 within tubular distal tip 52, as described hereinabove with reference to FIG. 1.

Figure 3B:
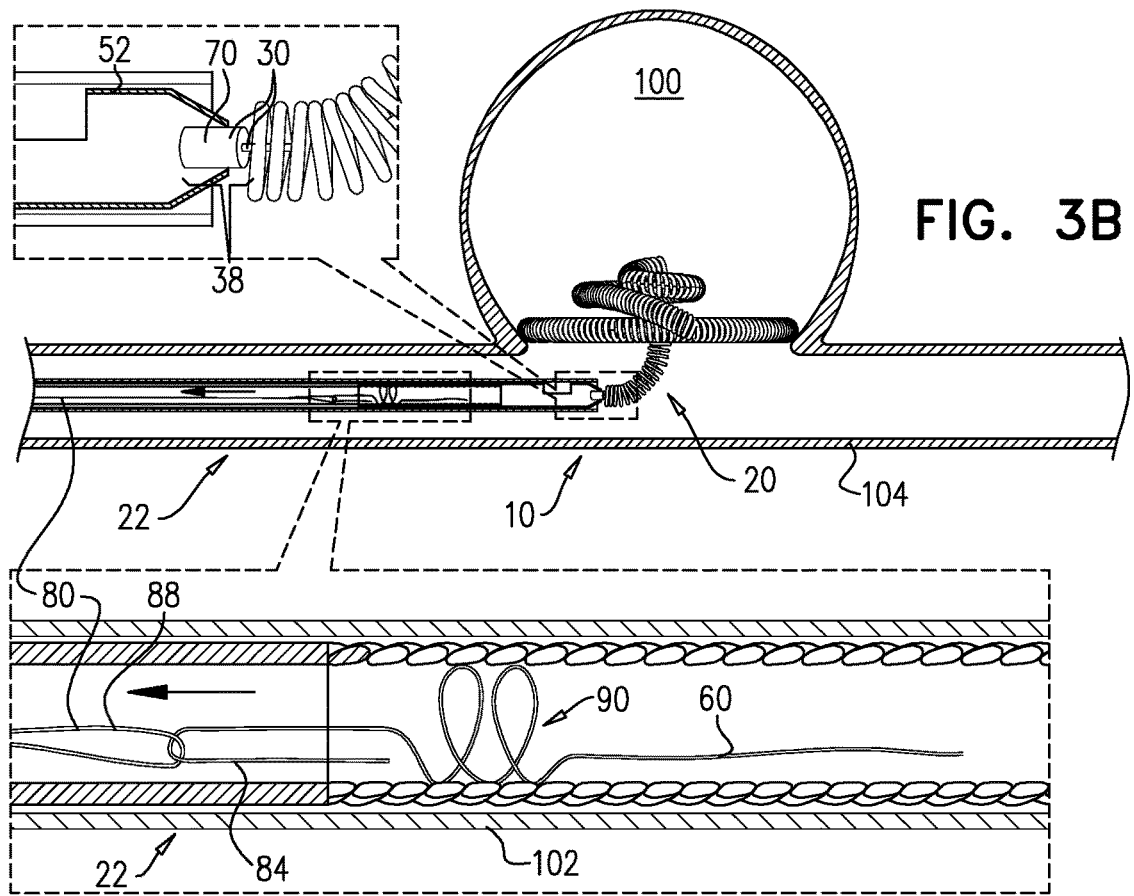

As shown in FIG. 3B, safety wire 60 is pulled proximally (i.e., to the left in the figures), which proximally retracts safety wire 60 from tip distal opening 56 of tubular distal tip 52, thereby allowing retention portion 38 to pass through tip distal opening 56, enabling releasing of implant 20 from delivery tool 22. As mentioned above, because tapered axial portion 58 of tubular distal tip 52 is smooth, it does not snag any sharp edges of retention portion 38, like a distal retention ring might, particularly for configurations in which retention portion 38 is cylindrical or otherwise has sharp edges.

Figure 3C:
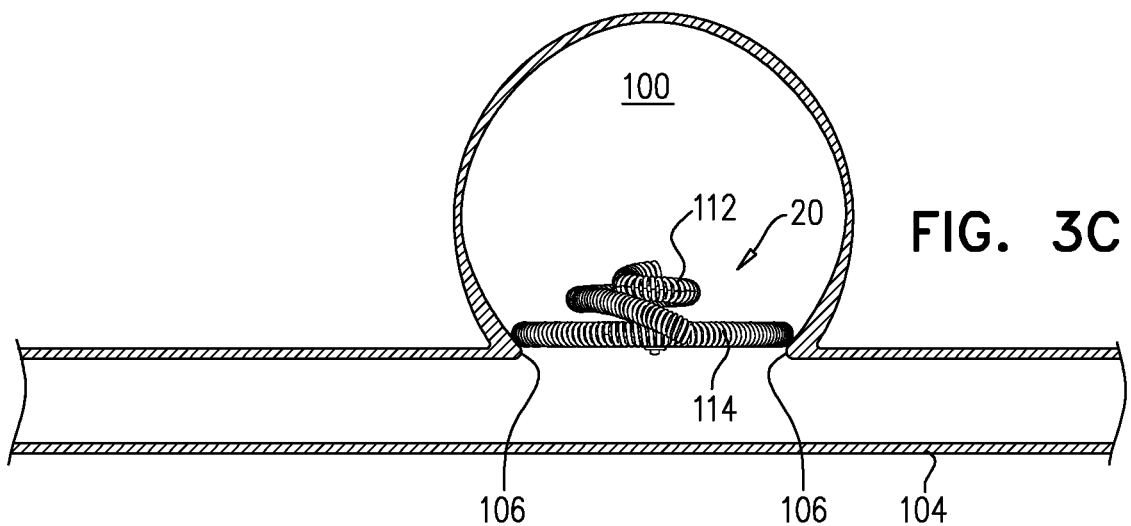

FIG. 3C shows implant 20 deployed in aneurysm 100 after delivery tool 22 and microcatheter 102 have been proximally withdrawn from blood vessel 104. In the particular configuration illustrated in FIGS. 3A-D, FIG. 3C shows an orifice section of implant 20 deployed within a portion of aneurysm 100, so as to at least partially cover an orifice 106 of aneurysm 100.

Figure 3D:
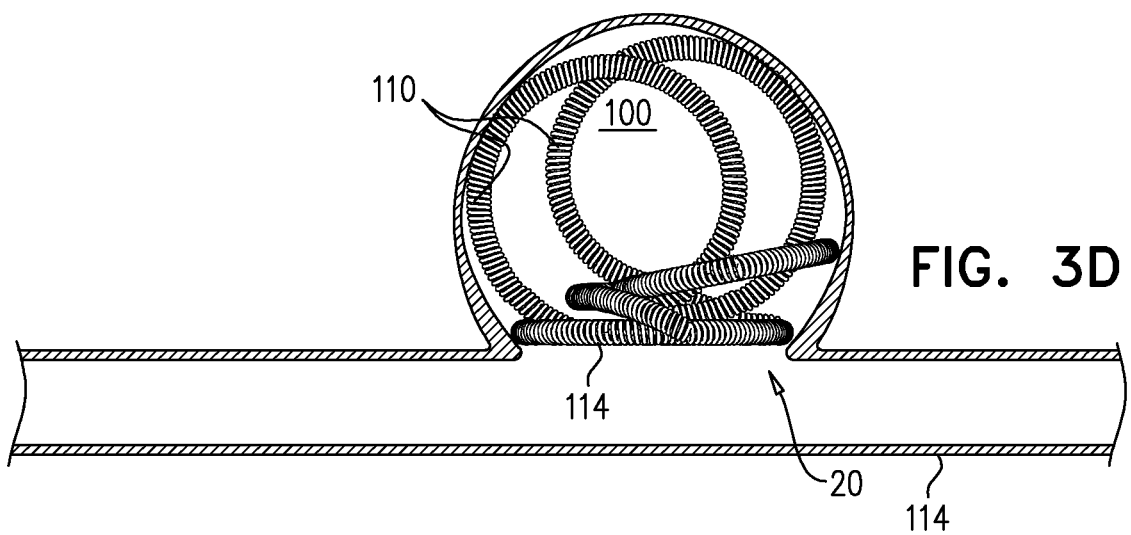

As shown in FIG. 3D, the method typically further comprises implanting endovascular embolization coils 110 in aneurysm 100, such that endovascular embolization coils 110 become entangled with an intra-vascular-malformation docking section 112 of implant 20. An orifice section 114 of implant 20 reduces the risk of (typically prevents) coil herniation, i.e., endovascular embolization coils 110 exiting the vascular malformation into the parent vessel, particularly in malformations with a wide opening such as wide-neck aneurysms and/or those located at bifurcations. The anatomy of wide-neck aneurysms often does not allow the aneurysmal sac to retain endovascular embolization coils 110 by itself, and herniating or protruding endovascular embolization coils can cause ischemic stroke.

Reference is now made to FIGS. 4A-E, which are schematic illustrations of a method for assembling implant system 10, in accordance with an application of the present invention.

Figure 4A:
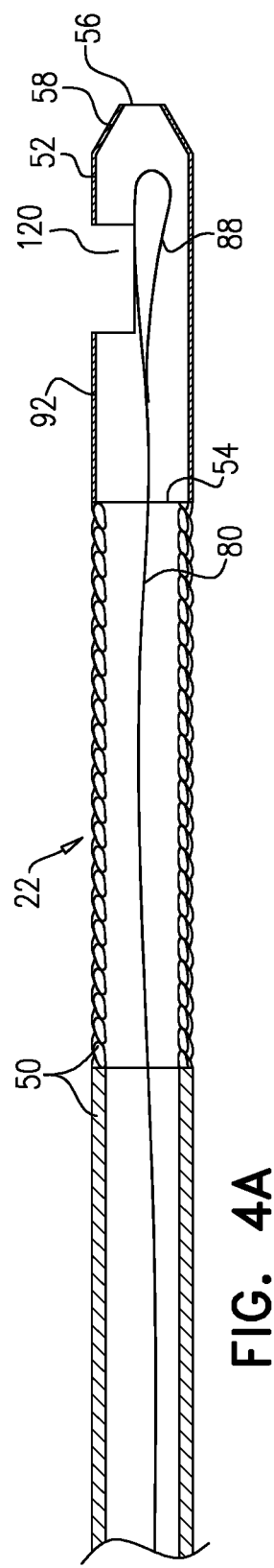
FIGS. 4A-E are schematic illustrations of a method for assembling the implant system of FIG. 1, in accordance with an application of the present invention.

As shown in FIG. 4A, pull wire 80 of delivery tool 22 is disposed partially within delivery tube 50 of delivery tool 22.

Figure 4B:
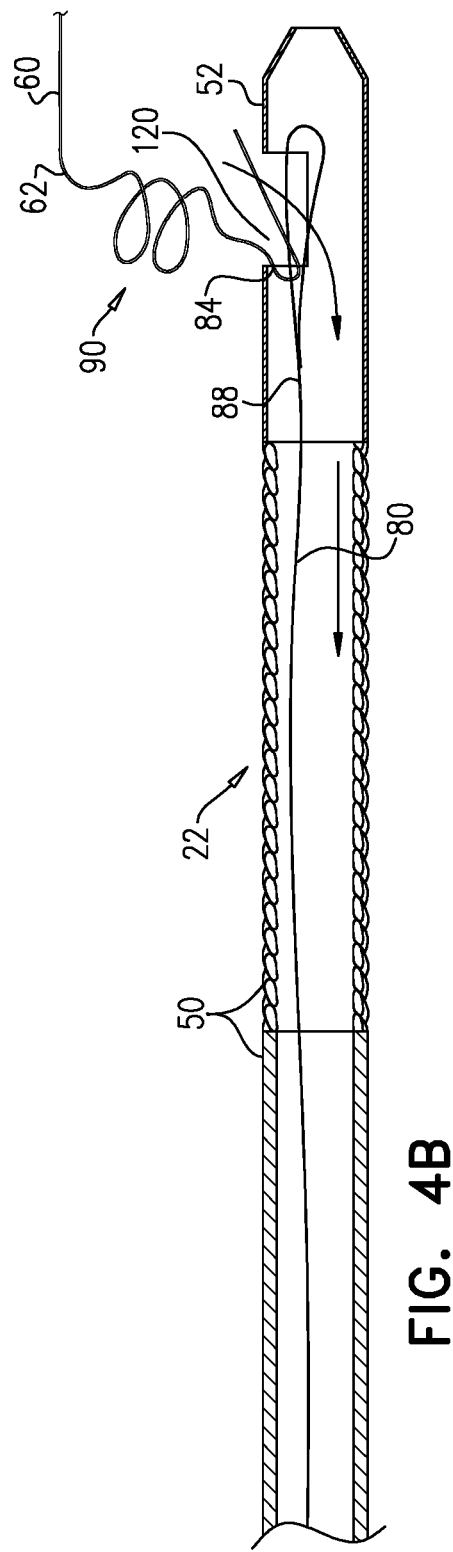

As shown in FIG. 4B, utilizing a lateral access window 120 defined by wall 92 of tubular distal tip 52, safety-wire hook 84 is hooked onto pull-wire loop 88. (As mentioned above, safety-wire hook 84 is defined by proximal end portion 82 of safety wire 60.)

For some applications, such as shown in FIG. 4B, safety-wire hook 84 is hooked onto pull-wire loop 88 while (a) pull wire 80 is partially disposed within delivery tube 50 and (b) pull-wire loop 88 and safety-wire hook 84 are disposed at least partially (e.g., entirely) inside delivery tool 22. Typically, safety-wire hook 84 is hooked onto pull-wire loop 88 while pull-wire loop 88 is at least partially axially aligned with lateral access window 120, in order to provide ready access to pull-wire loop 88 for the hooking.

Figure 4C:
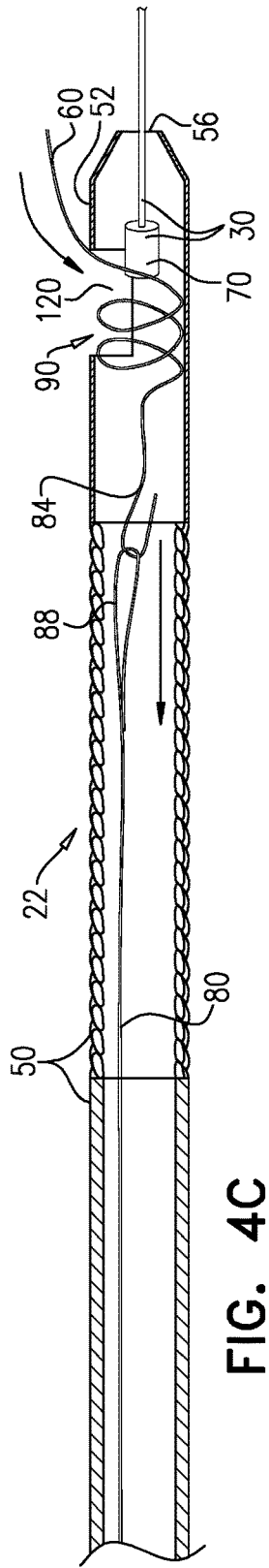

As shown in FIG. 4C, pull wire 80 is withdrawn proximally in order to draw safety wire 60 into tubular distal tip 52. As also shown in FIG. 4C, retention portion 38 of proximal end portion 34 of implant wire 30 of implant 20 is inserted through tip distal opening 56 of tubular distal tip 52 and into tubular distal tip 52. This step of the assembly method may optionally be performed earlier in the assembly method than illustrated, so long as retention portion 38 is inserted into tubular distal tip 52 before distal portion 62 of safety wire 60 is removably disposed through tip distal opening 56, as described below with reference to FIG. 4D.

Figure 4D:
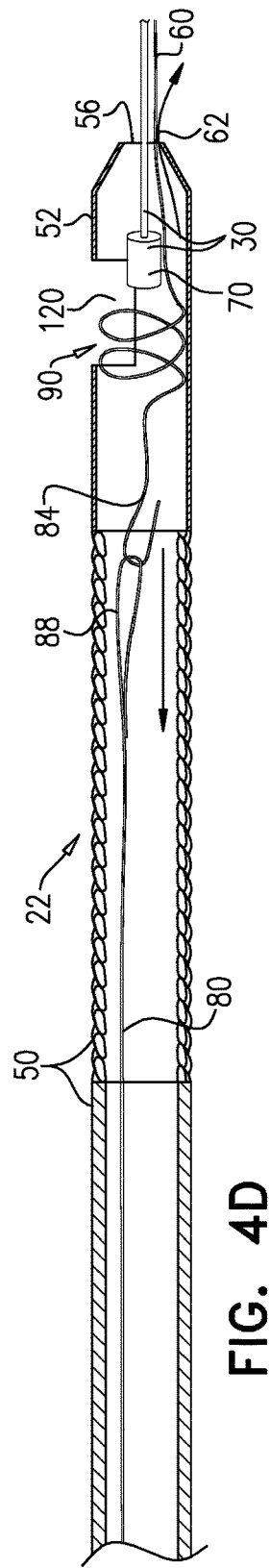
Figure 4E:
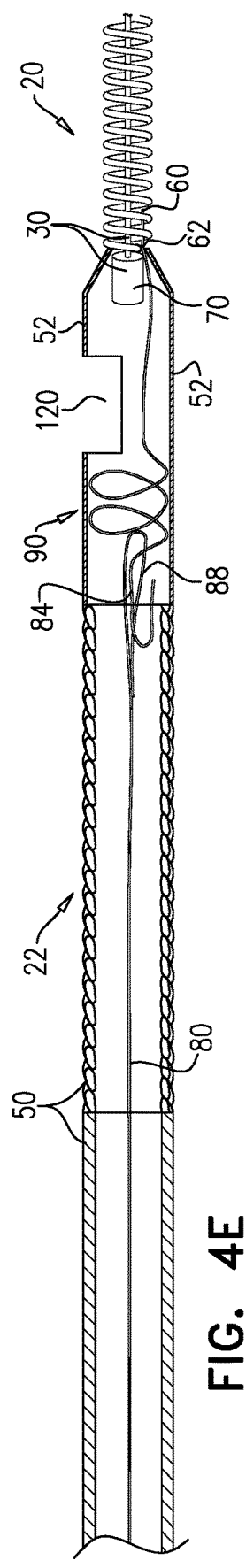

As shown in FIG. 4D, distal portion 62 of safety wire 60 is inserted through lateral access window 120 and into tubular distal tip 52, and distal portion 62 of safety wire 60 is removably disposed through tip distal opening 56 so as to effectively reduce a size of tip distal opening 56 to be too small for retention portion 38 to pass through, thereby retaining retention portion 38 within tubular distal tip 52, as shown in FIG. 4E.

Typically, such as shown in FIG. 4D, distal portion 62 of safety wire 60 is inserted through lateral access window 120 and into the tubular distal tip after hooking safety-wire hook 84 onto pull-wire loop 88. For other applications (not shown), distal portion 62 of safety wire 60 is inserted through lateral access window 120 and into the tubular distal tip before hooking safety-wire hook 84 onto pull-wire loop 88.

For some applications, such as shown in FIG. 4G, distal portion 62 of safety wire 60 is removably disposed through tip distal opening 56 and through portion of coil 40 alongside a portion of coil-wire portion 32 of implant wire 30. For some of these applications, the portion of safety wire 60 protruding from tip distal opening 56 is trimmed (e.g., to about 1 mm protruding from tip distal opening 56), to reduce the risk of safety wire 60 piercing the aneurysm, and then coil 40 is slid over safety wire 60.

Typically, pull-wire loop 88 is pushed distally (i.e., to the right in the figures), in order to provide the slack in pull-wire loop 88, as described hereinabove with reference to FIGS. 1 and 2C. Optionally, pull-wire loop 88 is pushed distally until further distal advancement is blocked by helical portion 90.

For some applications, tubular distal tip 52 comprises an internal stopper, which can be activated (i.e., pushed into the proximal path of retention portion 38 (e.g., retention element 70)) after retention portion 38 has been properly positioned during assembly of implant system 10, such that retention portion 38 can no longer move proximally. For example, the stopper may be defined by a small trap door in inner wall 92 of tubular distal tip 52 placed at an angle to central longitudinal axis 64 of tubular distal tip 52. Providing the stopper addresses a potential problem that when safety wire 60 is pulled proximally to allow releasing of retention portion 38 (and thus implant 20) from tubular distal tip 52, the retention portion 38 might be pulled proximally as well, instead of the desired distal motion of retention portion 38. However, during assembly of implant system 10, all proximal motion of retention portion 38 cannot be prevented, because retention portion 38 must be able to move proximally while safety wire 60 is advanced through tip distal opening 56.

In an embodiment, techniques and apparatus described in one or more of the following applications, which are assigned to the assignee of the present application and incorporated herein by reference, are combined with techniques and apparatus described herein:

U.S. Patent Application Publication 2017/0367708 to Mayer et al.
PCT Publication WO 2017/221252 to Mayer et al.
U.S. Provisional Application 62/785,013, filed Dec. 26, 2018
International Application PCT/IL2019/051401, filed Dec. 24, 2019

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An implant system comprising:
   (a) an implant, which comprises:
      (i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and
      (ii) a coil, which is coiled around the coil-wire portion and not the proximal end portion of the implant wire; and
   (b) a delivery tool, which comprises:
      (i) a delivery tube;
      (ii) a tubular distal tip, which is (A) fixed to a distal end of the delivery tube and (B) shaped so as to define a tip distal opening, wherein the retention portion is removably disposed within the tubular distal tip;
      (iii) a safety wire, which (A) has a proximal end portion that is shaped so as to define a safety-wire hook and (B) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip; and
      (iv) a pull wire, which (A) has a distal end portion that is shaped so as to define a pull-wire loop and (B) is removably disposed partially within the delivery tube, wherein the safety-wire hook is hooked on the pull-wire loop,
   wherein the implant system is configured such that proximal pulling on the pull wire proximally retracts the safety wire from the tip distal opening, thereby allowing the retention portion to pass through the tubular distal tip.

2. The implant system according to claim 1, wherein the safety wire is removably disposed partially within the tubular distal tip, with the distal portion of the safety wire passing through the tip distal opening and through a portion of the coil alongside a portion of the coil-wire portion of the implant wire.

3. The implant system according to claim 2, wherein a length of the portion of the coil-wire portion alongside which the safety wire passes is between 0.1 and 3 mm.

4. The implant system according to claim 1, wherein the safety wire is shaped so as to define a helical portion, which, when unconstrained, has an unconstrained helical-portion outer diameter that is greater than a greatest inner diameter of the tubular distal tip, such that the helical portion, when removably disposed within the tubular distal tip, pushes radially outwardly against an inner wall of the tubular distal tip.

5. The implant system according to claim 1, wherein the retention diameter equals at least 125% of the coil-wire-portion diameter.

6. The implant system according to claim 1, wherein the pull wire is coated with a non-stick coating and the safety wire is not coated with a non-stick coating.

7. The implant system according to claim 1, wherein a greatest outer diameter of the delivery tube is between 0.25 and 0.7 mm.

8. The implant system according to claim 1, wherein the tubular distal tip tapers toward the tip distal opening.

9. The implant system according to claim 1, wherein the coil has an outer dimeter of between 0.24 and 0.69 mm when unconstrained.

10. The implant system according to claim 1, wherein the implant comprises a retention element, which is fixed to the proximal end portion of the implant wire so as to define the retention portion having the retention diameter.

11. The implant system according to claim 10, wherein the retention element is cylindrical.

12. The implant system according to claim 11, wherein the cylindrical retention element has a length of between 0.2 and 0.8 mm and a diameter of between 0.12 and 0.55 mm.

13. The implant system according to claim 10, wherein the retention element is spherical.

14. The implant system according to claim 1, wherein the implant comprises an intravascular coil.

15. The implant system according to claim 1, wherein the implant comprises an orifice section; a docking section; and a connecting section, and wherein the implant is configured such that, when unconstrained, the orifice section is shaped so as to define an orifice-section curve, the docking section is shaped so as to define a docking-section curve, and the connecting section connects the orifice- section curve with the docking-section curve.

16. The implant system according to claim 1, wherein a distal-most point of the pull-wire loop is initially disposed a distance distal to a proximal-most point of the safety-wire hook, such that proximal pulling of the pull wire by up to the distance is not transmitted to the distal portion of the safety wire.

17. The implant system according to claim 16, wherein the distance is at least 1 mm.

18. The implant system according to claim 1, wherein an inner wall of the tubular distal tip defines a lateral access window.

19. A method for treating a vascular malformation, the method comprising:
inserting a microcatheter into a blood vessel while a delivery tool and an implant of an implant system are removably disposed in the microcatheter, with a proximal end of the implant removably coupled to a tubular distal tip of the delivery tool, wherein the implant includes (i) an implant wire, which includes (A) a coil-wire portion having a coil-wire-portion diameter and (B) a proximal end portion that (1) includes a proximal end of the implant wire, (2) is non-axially-overlapping with the coil-wire portion, and (3) includes a retention portion that has a retention diameter that is greater than the coil-wire-portion diameter; and (ii) a coil, which is coiled around the coil-wire portion and not the proximal end portion of the implant wire, and wherein the delivery tool includes (i) a delivery tube; (ii) a tubular distal tip, which is (A) fixed to a distal end of the delivery tube and (B) shaped so as to define a tip distal opening, wherein the retention portion is removably disposed within the tubular distal tip; (iii) a safety wire, which (A) has a proximal end portion that is shaped so as to define a safety-wire hook and (B) is removably disposed partially within the tubular distal tip, with a distal portion of the safety wire passing through the tip distal opening so as to effectively reduce a size of the tip distal opening to be too small for the retention portion to pass through, thereby retaining the retention portion within the tubular distal tip; and (iv) a pull wire, which (A) has a distal end portion that is shaped so as to define a pull-wire loop and (B) is removably disposed partially within the delivery tube, wherein the safety-wire hook is hooked on the pull-wire loop;

advancing the microcatheter in the blood vessel toward the vascular malformation;

deploying the implant from the microcatheter into the vascular malformation; and releasing the implant from the delivery tool by proximally pulling on the safety wire so as to proximally retract the safety wire from the tip distal opening of the tubular distal tip, thereby allowing the retention portion to pass through the tip distal opening.

20. The method according to claim 19, wherein a distal-most point of the pull-wire loop is initially disposed a distance distal to a proximal-most point of the safety-wire hook, such that proximal pulling of the pull wire by up to the distance is not transmitted to the distal portion of the safety wire.

* * * * *